(12) United States Patent
Hietpas

(10) Patent No.: US 8,044,258 B2
(45) Date of Patent: Oct. 25, 2011

(54) ABSORBENT ARTICLE FEATURING LEAKAGE WARNING

(75) Inventor: Lloyd Carl Hietpas, Kimberly, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 384 days.

(21) Appl. No.: 12/215,444

(22) Filed: Jun. 27, 2008

(65) Prior Publication Data

US 2009/0326492 A1 Dec. 31, 2009

(51) Int. Cl.
*A61F 13/15* (2006.01)

(52) U.S. Cl. ........ 604/361; 604/362; 604/367; 604/378; 604/385.28

(58) Field of Classification Search ............ 604/361, 604/362, 367, 385.01, 378, 385.28
See application file for complete search history.

(56) References Cited

U.S. PATENT DOCUMENTS

| | | |
|---|---|---|
| 3,794,024 A | 2/1974 | Kokx et al. |
| 3,849,241 A | 11/1974 | Butin et al. |
| 4,289,794 A | 9/1981 | Kleiner et al. |
| 4,340,563 A | 7/1982 | Appel et al. |
| 4,405,297 A | 9/1983 | Appel et al. |
| 4,639,949 A | 2/1987 | Ales et al. |
| 4,699,823 A | 10/1987 | Kellenberger et al. |
| 4,704,116 A | 11/1987 | Enloe |
| 4,940,464 A | 7/1990 | Van Gompel et al. |
| 5,114,781 A | 5/1992 | Morman |
| 5,116,662 A | 5/1992 | Morman |
| 5,147,343 A | 9/1992 | Kellenberger |
| 5,266,592 A | 11/1993 | Grub et al. |
| 5,348,750 A | 9/1994 | Greenberg |
| 5,486,166 A | 1/1996 | Bishop et al. |
| 5,490,846 A | 2/1996 | Ellis et al. |
| 5,557,263 A | 9/1996 | Fisher et al. |
| 5,645,542 A | 7/1997 | Anjur et al. |
| 5,649,914 A | 7/1997 | Glaug et al. |
| 5,681,298 A | 10/1997 | Brunner et al. |
| 5,702,376 A | 12/1997 | Glaug et al. |
| 5,728,125 A | 3/1998 | Salinas |
| 5,760,694 A * | 6/1998 | Nissim et al. ............ 340/604 |
| 5,797,892 A | 8/1998 | Glaug et al. |
| 5,883,028 A | 3/1999 | Morman et al. |
| 5,904,671 A | 5/1999 | Navot et al. |
| 5,964,743 A | 10/1999 | Abuto et al. |
| 6,045,900 A | 4/2000 | Haffner et al. |
| 6,231,557 B1 | 5/2001 | Krautkramer et al. |
| 6,246,330 B1 | 6/2001 | Nielsen |
| 6,315,765 B1 | 11/2001 | Datta et al. |
| 6,348,640 B1 | 2/2002 | Navot et al. |

(Continued)

FOREIGN PATENT DOCUMENTS

EP  1 250 940 A1  10/2002

(Continued)

*Primary Examiner* — Jacqueline F. Stephens
(74) *Attorney, Agent, or Firm* — Randall W. Fieldback

(57) ABSTRACT

An absorbent article for preventing leakage is presented and includes an absorbent assembly having an absorbent assembly perimeter and a leakage warning element disposed adjacent a portion of the perimeter, wherein the leakage warning element is adapted to provide a physical sensation indicating a fullness level of the absorbent assembly, and wherein the physical sensation includes an electrical impulse. Also presented is an absorbent article for providing a wearer with a warning of potential leakage, the article including an absorbent assembly and a leakage warning element disposed adjacent the absorbent assembly, wherein the leakage warning element is adapted to impart a physical sensation to the wearer, and wherein the physical sensation includes an electrical impulse.

20 Claims, 5 Drawing Sheets

U.S. PATENT DOCUMENTS

| | | | |
|---|---|---|---|
| 6,362,389 | B1 | 3/2002 | McDowall et al. |
| 6,372,951 | B1 | 4/2002 | Ter-Ovanwsyan et al. |
| 6,373,395 | B1 | 4/2002 | Kimsey |
| 6,387,084 | B1 | 5/2002 | VanGompel et al. |
| 6,506,958 | B2 | 1/2003 | Williams |
| 6,552,245 | B1 | 4/2003 | Roessler et al. |
| 6,559,772 | B2 | 5/2003 | Zand et al. |
| 6,576,810 | B1 | 6/2003 | Underhill et al. |
| 6,583,722 | B2 | 6/2003 | Jeutter et al. |
| 6,596,919 | B2 | 7/2003 | Williams |
| 6,603,403 | B2 | 8/2003 | Jeutter et al. |
| 6,642,427 | B2 | 11/2003 | Roe et al. |
| 6,677,859 | B1 | 1/2004 | Bensen |
| 6,972,010 | B2 | 12/2005 | Pesce et al. |
| 7,002,055 | B2 | 2/2006 | Long et al. |
| 7,250,548 | B2 | 7/2007 | Weber et al. |
| 2001/0049513 | A1 | 12/2001 | Neading et al. |
| 2003/0120227 | A1 | 6/2003 | Williams |
| 2003/0139291 | A1 | 7/2003 | Qin |
| 2004/0030310 | A1 | 2/2004 | Roe et al. |
| 2004/0064114 | A1 | 4/2004 | David et al. |
| 2004/0064116 | A1 | 4/2004 | Arora et al. |
| 2004/0081680 | A1 | 4/2004 | Pesce et al. |
| 2004/0082928 | A1 | 4/2004 | Pesce et al. |
| 2004/0128153 | A1 | 7/2004 | Zhang et al. |
| 2004/0254549 | A1 | 12/2004 | Olson et al. |
| 2004/0254550 | A1 | 12/2004 | Huang et al. |
| 2005/0124947 | A1 | 6/2005 | Fernfors |
| 2005/0137561 | A1 | 6/2005 | Mizutani et al. |
| 2006/0069363 | A1 | 3/2006 | Weber et al. |
| 2006/0105963 | A1 | 5/2006 | Yang et al. |
| 2006/0142713 | A1 | 6/2006 | Long et al. |
| 2006/0142714 | A1 | 6/2006 | Jackson et al. |
| 2006/0142715 | A1 | 6/2006 | Long et al. |
| 2006/0142716 | A1 | 6/2006 | Long et al. |
| 2006/0149197 | A1 | 7/2006 | Niemeyer |
| 2006/0247588 | A1 | 11/2006 | Olson et al. |
| 2007/0049881 | A1 | 3/2007 | Ales et al. |
| 2007/0049882 | A1 | 3/2007 | Long et al. |
| 2007/0049883 | A1 | 3/2007 | Ales et al. |
| 2007/0083173 | A1 | 4/2007 | Olson |
| 2007/0088303 | A1 | 4/2007 | Olson et al. |
| 2007/0142799 | A1 | 6/2007 | Ales et al. |
| 2007/0149936 | A1 | 6/2007 | Weber et al. |
| 2007/0252710 | A1 | 11/2007 | Long et al. |
| 2007/0252711 | A1 | 11/2007 | Long et al. |
| 2008/0058742 | A1 | 3/2008 | Ales |
| 2008/0134487 | A1 | 6/2008 | Hartono |
| 2009/0157022 | A1 | 6/2009 | MacDonald et al. |

FOREIGN PATENT DOCUMENTS

| | | | |
|---|---|---|---|
| EP | 1 250 914 B1 | 5/2006 | |
| EP | 1 342 219 B1 | 6/2007 | |
| GB | 1 433 415 A | 4/1976 | |
| WO | WO 94/22401 A1 | 10/1994 | |
| WO | WO 01/95845 A1 | 12/2001 | |
| WO | WO 03/002049 A1 | 1/2003 | |
| WO | WO 03/051254 A2 | 6/2003 | |
| WO | WO 2007/027259 A1 | 3/2007 | |
| WO | WO 2007/027266 A1 | 3/2007 | |
| WO | WO 2007/069945 A1 | 6/2007 | |
| WO | WO 2007/077538 A1 | 7/2007 | |
| WO | WO 2007/087674 A1 | 8/2007 | |
| WO | WO 2008/020347 A1 | 2/2008 | |

* cited by examiner

ABSORBENT ARTICLE FEATURING LEAKAGE WARNING

BACKGROUND

The present disclosure relates to absorbent articles that include a leakage warning element. More specifically, the disclosure relates to an absorbent article such as feminine care products, incontinence products, and training pants that provides the wearer with a noticeable physical sensation when the absorbent article is reaching fullness and prior to potential leakage from the absorbent article.

Absorbent articles such as feminine care products, incontinence products, and training pants are useful to absorb and contain body wastes. These products have developed to the extent that body exudates are quickly drawn and retained away from the wearer's skin so that the wearer remains relatively dry and comfortable. Although this improved performance enhances wearer dryness and comfort, it can reduce the wearer's ability to notice or recognize when the article is becoming full, especially if the wearer's attention is distracted by an activity. In one example, all adult care product wearers, especially women, are very concerned about leakage in public. Some wearers can be so bothered by leakage that if it occurs in a public place, they will avoid that place and situation for the rest of their life. Leakage is therefore absolutely taboo in an adult care product. Similar circumstances can apply to feminine care products and training pants as well.

This application teaches products and methods to sense and inform an absorbent article wearer when leakage is about to occur so that the absorbent article wearer can reliably avoid leakage.

SUMMARY

In response to the discussed deficiencies in the prior art, a new absorbent article has been developed. Absorbent articles of the present disclosure provide a physical sensation upon contact with urine or other body exudates once the urine or other body exudates has nearly filled the absorbent article. As a result, the wearer will notice a distinct physical sensation to assist the wearer in recognizing when the absorbent article is nearing fullness.

In one aspect of the present disclosure, an absorbent article for preventing leakage includes an absorbent assembly having an absorbent assembly perimeter and a leakage warning element disposed adjacent a portion of the perimeter, wherein the leakage warning element is adapted to provide a physical sensation indicating a fullness level of the absorbent assembly.

In another aspect of the present disclosure, an absorbent article provides a wearer with a warning of potential leakage, the article including an absorbent assembly and a leakage warning element disposed adjacent the absorbent assembly, wherein the leakage warning element is adapted to impart a physical sensation to the wearer.

In another aspect of the present disclosure, absorbent article provides a wearer with a warning of potential leakage, the article including an absorbent assembly and a leakage warning element in fluid contact with the absorbent assembly, wherein the leakage warning element is adapted to impart a physical sensation to the wearer.

The purposes and features of the present disclosure will be set forth in the description that follows. Additional features of the disclosure can be realized and attained by the product and processes particularly pointed out in the written description and claims hereof, as well as from the appended drawings.

It is to be understood that both the foregoing general description and the following detailed description are exemplary and are intended to provide further explanation of the disclosure claimed. The accompanying drawings, which are incorporated in and constitute part of this specification, are included to illustrate and provide a further understanding of the disclosure.

BRIEF DESCRIPTION OF THE DRAWINGS

The present disclosure will be more fully understood, and further features will become apparent, when reference is made to the following detailed description and the accompanying drawings. The drawings are merely representative and are not intended to limit the scope of the claims.

Figure 1:
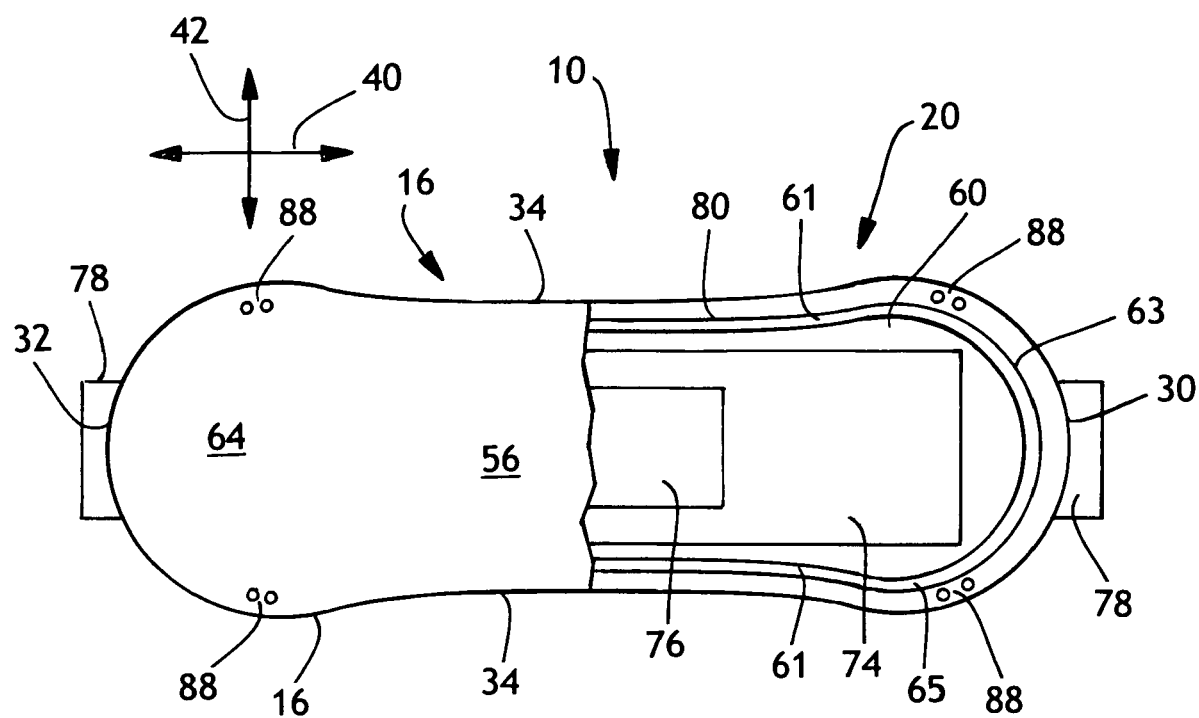
FIG. 1 representatively illustrates a plan view of a feminine/incontinence pad of the present disclosure showing the surface of the feminine/incontinence pad that faces the wearer when worn, and with portions cut away to show underlying features.

Repeat use of reference characters in the present specification and drawings is intended to represent the same or analogous features or elements of the present disclosure. The drawings are representational and are not necessarily drawn to scale. Certain proportions thereof can be exaggerated, while others can be minimized.

DETAILED DESCRIPTION

Within the context of this specification, each term or phrase below includes the following meaning or meanings:

"Attach" and its derivatives refer to the joining, adhering, connecting, bonding, sewing together, or the like, of two elements. Two elements will be considered to be attached together when they are integral with one another or attached directly to one another or indirectly to one another, such as when each is directly attached to intermediate elements. "Attach" and its derivatives include permanent, releasable, or refastenable attachment. In addition, the attachment can be completed either during the manufacturing process or by the end wearer.

"Bond" and its derivatives refer to the joining, adhering, connecting, attaching, sewing together, or the like, of two elements. Two elements will be considered to be bonded together when they are bonded directly to one another or indirectly to one another, such as when each is directly bonded to intermediate elements. "Bond" and its derivatives include permanent, releasable, or refastenable bonding.

"Connect" and its derivatives refer to the joining, adhering, bonding, attaching, sewing together, or the like, of two elements. Two elements will be considered to be connected together when they are connected directly to one another or indirectly to one another, such as when each is directly connected to intermediate elements. "Connect" and its derivatives include permanent, releasable, or refastenable connection. In addition, the connecting can be completed either during the manufacturing process or by the end wearer.

"Disposable" refers to articles which are designed to be discarded after a limited use rather than being laundered or otherwise restored for reuse.

"Join" and its derivatives refer to the connecting, adhering, bonding, attaching, sewing together, or the like, of two elements. Two elements will be considered to be joined together when they are integral with one another or joined directly to one another or indirectly to one another, such as when each is directly joined to intermediate elements. "Join" and its derivatives include permanent, releasable, or refastenable joiner. In addition, the joining can be completed either during the manufacturing process or by the end wearer.

"Layer" when used in the singular can have the dual meaning of a single element or a plurality of elements.

These terms can be defined with additional language in the remaining portions of the specification.

While a leakage warning element 20 is illustrated in FIG. 1 with a feminine care product, the leakage warning element 20 can also be used in conjunction with other garments. For example, a leakage warning element 20 of the disclosure can be used with other disposable absorbent articles such as diapers, diaper pants, training pants, incontinence articles, feminine pads, liners, and tampons, or the like. The descriptions of the various absorbent articles 10 described herein are for exemplary purposes only. Variations in the structures, materials, and designs of the absorbent articles 10 that do not impact the subject matter of this disclosure are possible and expected.

The present disclosure can be applied to a feminine/incontinence pad 16, as illustrated in FIG. 1. The exemplary feminine/incontinence pad 16 includes an outercover (otherwise referred to as a baffle or backsheet, not shown), an absorbent assembly 60, an optional tissue layer 74, an optional distribution layer (surge layer) 76 and a bodyside liner 64 (also referred to as the topsheet). The feminine/incontinence pad 16 also has first and second side edges 34 that are the longitudinal sides of the elongated feminine/incontinence pad 16. The side edges 34 can be contoured, for example, in a concave shape, or they can be linear. The sides can further include flaps (not shown) that extend laterally outward. In one embodiment (not shown), one or more elastic elements are disposed along the sides to form a gasket with the body of the wearer. In one embodiment, the elastic elements are disposed between the bodyside liner 64 and the outercover.

The feminine/incontinence pad 16 has a bodyside inner surface 56 and a garment-side outer surface. Applied to at least a portion of the garment-side outer surface is a garment attachment adhesive. In various embodiments, the garment attachment adhesive is configured as a single band of adhesive or as two or more spaced apart strips. Alternatively, the garment attachment adhesive can include a swirl pattern of adhesive which encompasses a major portion of the garment-side outer surface of the feminine/incontinence pad 16.

A release strip 78, also known as a releasable peel strip, is removably secured to the garment attachment adhesive and serves to prevent premature contamination of the adhesive before the feminine/incontinence pad 16 is secured to the crotch portion of an undergarment. In various embodiments, the garment attachment adhesive is designed to be secured to the inner crotch portion of an undergarment so as to keep the absorbent product in register with the body of the wearer. The release strip 78 can extend beyond one or both of the end edges 30, 32 of the outercover, as shown in FIG. 1. Alternatively, the release strip 78 can be as short as the length of the garment attachment adhesive, or slightly longer than the adhesive or can be only as long as the garment attachment adhesive, but does not extend beyond the end edges 30, 32 of the outercover.

The body-side liner or topsheet 64, which is preferably liquid permeable, can be formed from one or more materials. The body-side liner or topsheet 64 must be able to manage different body excretions depending on the type of product. In feminine care products, often the body-side liner or body-contacting layer 64 must be able to handle menses and urine. In the present disclosure, the body-side liner or topsheet 64 can include a layer constructed of any operative material, and can be a composite material. For example, the body-side liner or body-contacting layer 64 can include a woven fabric, a nonwoven fabric, a polymer film, a film-nonwoven fabric laminate or the like, as well as combinations thereof. Examples of a nonwoven fabric useable in the body-side liner or topsheet 64 include, for example, an airlaid nonwoven web, a spunbond nonwoven web, a meltblown nonwoven web, a bonded-carded-web, a hydroentangled nonwoven web, a spunlace web or the like, as well as combinations thereof. Other examples of suitable materials for constructing the body-side liner or topsheet 64 can include rayon, bonded-carded-webs of polyester, polypropylene, polyethylene, nylon, or other heat-bondable fibers finely perforated film webs, net-like materials, and the like, as well as combinations thereof. These webs can be prepared from polymeric materials such as, for example, polyolefins, such as polypropylene and polyethylene and copolymers thereof, polyesters in general including aliphatic esters such as polylactic acid, nylon or any other heat-bondable materials.

Other examples of suitable materials for the body-side liner or topsheet 64 are composite materials of a polymer and a nonwoven fabric material. The composite materials are typically in the form of integral sheets generally formed by the extrusion of a polymer onto a nonwoven web, such as a spunbond material. In a desired arrangement, the liner or body contacting layer 64 can be configured to be operatively liquid-permeable with regard to the liquids that the article is intended to absorb or otherwise handle. The operative liquid-permeability may, for example, be provided by a plurality of pores, perforations, apertures or other openings, as well as combinations thereof, which are present or formed in the liner or body contacting layer. The apertures or other openings can help increase the rate at which bodily liquids can move through the thickness of the liner or body contacting layer and penetrate into the other components of the article (e.g. into the absorbent assembly 60). The selected arrangement of liquid-permeability is desirably present at least on an operative portion of the body-side liner or topsheet 64 that is appointed for placement on the body-side of the article. The body-side liner or topsheet 64 can provide comfort and conformability, and can function to direct bodily exudates away from the body and toward the absorbent assembly 60. The body-side liner or topsheet 64 can be configured to retain little or no liquid in its structure, and can be configured to provide a relatively comfortable and non-irritating surface next to the body tissues of a wearer. In the present invention, the topsheet or body-facing surface of each absorbent article can be embossed, printed or otherwise imparted with a pattern.

The outercover can include a layer constructed of any operative material, and can or can not have a selected level of liquid-permeability or liquid-impermeability, as desired. In a particular configuration, the outercover can be configured to provide an operatively liquid-impermeable baffle structure. The outercover may, for example, include a polymeric film, a woven fabric, a nonwoven fabric or the like, as well as combinations or composites thereof. For example, the outercover can include a polymer film laminated to a woven or nonwoven fabric. In a particular feature, the polymer film can be composed of polyethylene, polypropylene, polyester or the like, as well as combinations thereof. Additionally, the polymer film can be micro-embossed, have a printed design, have a printed message to the consumer, and/or can be at least partially colored. Suitably, the outercover can operatively permit a sufficient passage of air and moisture vapor out of the article, particularly out of an absorbent (e.g. storage or absorbent assembly 60) while blocking the passage of bodily liquids.

Bicomponent films or other multi-component films can also be used, as well as woven and/or nonwoven fabrics which have been treated to render them operatively liquid-impermeable. Another suitable outercover material can include a closed cell polyolefin foam. For example, a closed-cell polyethylene foam can be employed.

The liquid permeable body-side liner 64 and the liquid-impermeable outercover can be peripherally sealed together to enclose the absorbent assembly 60 to form the feminine/incontinence pad 16. Alternatively, the body-side liner or topsheet 64 can be wrapped around both the absorbent assembly 60 and the outercover to form a wrapped pad. The body-side liner 64 and outercover, and other components of the feminine/incontinence pad 16, can be joined for example with adhesive bonds, sonic bonds, thermal bonds, pinning, stitching or any other attachment techniques known in the art, as well as combinations thereof.

The absorbent assembly 60 can be in a variety of shapes and configurations as are known in the art, such as rectangular, hourglass shaped, I-shaped, and the like. The absorbent assembly 60 has opposed lateral edges 61 and opposed longitudinal ends 63. The lateral edges 61 and longitudinal ends 63 together make up the perimeter 65 of the absorbent assembly 60.

The absorbent assembly 60 is designed to absorb body exudates, including menstrual fluid, blood, urine, and other body fluids. The absorbent assembly 60 can contain one or more layers of absorbent material. The layers can contain similar materials or different materials. Suitable materials for the absorbent assembly 60 include, for example, cellulose, wood pulp fluff, rayon, cotton, and meltblown polymers such as polyester, polypropylene or coform. Coform is a meltblown air-formed combination of meltblown polymers, such as polypropylene, and absorbent staple fibers, such as cellulose. A preferred material is wood pulp fluff, for it is low in cost, relatively easy to form, and has good absorbency.

The absorbent assembly 60 can also be formed from a composite including a hydrophilic material which can be formed from various natural or synthetic fibers, wood pulp fibers, regenerated cellulose or cotton fibers, or a blend of pulp and other fibers. A desired material is an airlaid material.

In one embodiment, the absorbent assembly 60 also includes a superabsorbent material, in addition to or in place of the hydrophilic material, which increases the ability of the absorbent core to absorb a large amount of fluid in relation to its own weight. Generally stated, the superabsorbent material can be a water-swellable, generally water-insoluble, hydrogel-forming polymeric absorbent material, which is capable of absorbing at least about 15, suitably about 30, and possibly about 60 times or more its weight in physiological saline (e.g. saline with 0.9 wt % NaCl). The superabsorbent materials can be inserted as particles or in sheet form. The superabsorbent material can be biodegradable or bipolar. The hydrogel-forming polymeric absorbent material can be formed from organic hydrogel-forming polymeric material, which can include natural material such as agar, pectin, and guar gum; modified natural materials such as carboxymethyl cellulose, carboxyethyl cellulose, and hydroxypropyl cellulose; and synthetic hydrogel-forming polymers. Synthetic hydrogel-forming polymers include, for example, alkali metal salts of polyacrylic acid, polyacrylamides, polyvinyl alcohol, ethylene maleic anhydride copolymers, polyvinyl ethers, polyvinyl morpholinone, polymers and copolymers of vinyl sulfonic acid, polyacrylates, polyacrylamides, polyvinyl pyridine, and the like. Other suitable hydrogel-forming polymers include hydrolyzed acrylonitrile grafted starch, acrylic acid grafted starch, and isobutylene maleic anhydride copolymers and mixtures thereof. The hydrogel-forming polymers can be lightly crosslinked to render the material substantially water insoluble. Crosslinking may, for example, be by irradiation or covalent, ionic, Van der Waals, or hydrogen bonding. Hydroxyfunctional polymers have been found to be good superabsorbents for sanitary napkins. Such superabsorbents are a partially neutralized salt of cross-linked copolymer of polyacrylic acid and polyvinyl alcohol having an absorbency under load value above 25 grams of absorbed liquid per gram of absorbent material (g/g). Other types of superabsorbent materials known to those skilled in the art can also be used.

Additional layers or substrates, including for example, the liquid acquisition and distribution layer 76, also referred to as a surge or transfer layer, and an optional tissue layer 74 can also be incorporated into the feminine/incontinence pad 16.

The leakage warning element 20 is positioned within the feminine/incontinence pad 16 so that menses or other body exudates filling the absorbent assembly 60 contacts the leakage warning element 20 prior to completely filling and eventually leaking from the feminine/incontinence pad 16. Thus, the leakage warning element 20 is disposed with or near the absorbent assembly 60 so that menses or other body exudates contacting the absorbent assembly will also eventually contact the leakage warning element 20. Most desirably, the leakage warning element 20 is disposed on the bodyside of the absorbent assembly 60 so as to be sandwiched between the absorbent assembly 60 and the bodyside liner 64. In this way, the physical sensation resulting from the leakage warning element 20 is more easily noticed by the wearer. In one aspect of the present disclosure, the physical sensation provided by the leakage warning element 20 can be an electrical impulse, which might be described by the wearer as a tingle, a tickle, or a prickling sensation.

Generally, the closer to the perimeter of the absorbent assembly the leakage warning element 20 is placed, the less time a wearer will have to change the article 10 before a leak can occur. The remaining time available to a wearer is also dependent on other factors including the nature of the bodily waste captured in the absorbent assembly. For example, the rate of flow of menses in an absorbent assembly is generally slower than the rate of flow of urine in an absorbent assembly.

Alternatively, however, the leakage warning element 20 can be located within the absorbent assembly 60 or beneath the absorbent assembly 60 (not shown). The leakage warning element 20 can also be positioned on the flaps or in any other suitable position in the feminine/incontinence pad 16, as long as fluid communication is provided between the absorbent assembly 60 and the leakage warning element 20. In addition, leakage warning elements 20 can be positioned in more than one location within the feminine/incontinence pad 16. The leakage warning element 20 can be bonded in position using adhesives, ultrasonic bonds, or other suitable means.

One or more leakage warning elements 20 can be disposed in the feminine/incontinence pad 16. A pair of leakage warning elements 20 can be positioned on opposite sides of the longitudinal axis 40 and spaced apart from the intersection of the longitudinal and transverse axes 40, 42 along the transverse axis 42. Similarly, a pair of leakage warning elements 20 can be positioned on opposite sides of the transverse axis 42 and spaced apart from the intersection of the longitudinal and transverse axes 40, 42 along the longitudinal axis 40. In another aspect, leakage warning elements 20 can be positioned at each of the points at which an axis meets the perimeter 65 of the absorbent assembly 60. In still another aspect, the leakage warning elements 20 can be positioned completely or partially along the entire absorbent assembly perimeter 65.

The position and/or structure of the leakage warning elements 20 should be such that the leakage warning elements 20 come in contact with urine or other bodily waste as the absorbent assembly 60 fills but prior to any leakage from the absorbent assembly 60. The leakage warning element(s) 20 can be centered in the longitudinal direction 40. Alternatively, however, the leakage warning element(s) 20 can be located off the transverse axis 40 of the feminine/incontinence pad 16. Likewise, the leakage warning element(s) 20 can be centered in the transverse direction 42 or can be located off the longitudinal axis 42 of the feminine/incontinence pad 16.

In use, the leakage warning element 20 in the feminine care product 12 is designed to draw the wearer's attention to the fact that the absorbent assembly is nearing fullness. Depending on the particular type of leakage warning element 20 used, the leakage warning element 20 will produce a physical sensation. As a result, the wearer will experience that physical sensation when the absorbent assembly is approaching fullness to indicate to the wearer that potential leakage is imminent.

As noted previously, the leakage warning element 20 is positioned and adapted to create a distinct physical sensation upon the absorbent article 10 approaching fullness. As the absorbent assembly 60 fills with menses or other body exudates, the menses or other body exudates encounters the leakage warning element 20 where the menses or other body exudates initiates a physical sensation that can be felt by the wearer of the absorbent article 10, thus alerting the wearer that a leak can soon occur.

Figure 2:
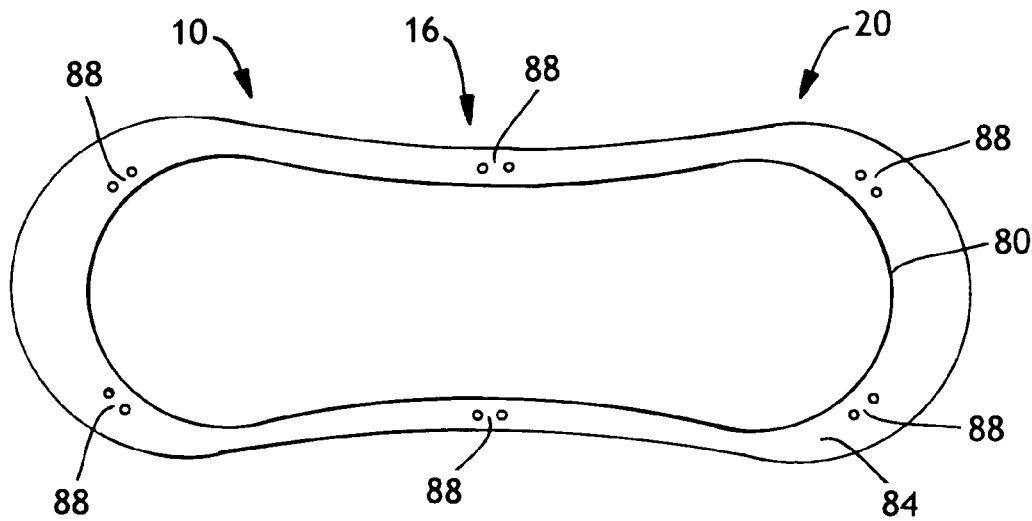
FIG. 2 representatively illustrates a plan schematic view of a particular aspect of the leakage warning element viewed from the top as used in conjunction with the feminine/incontinence pad of FIG. 1.
Figure 3:
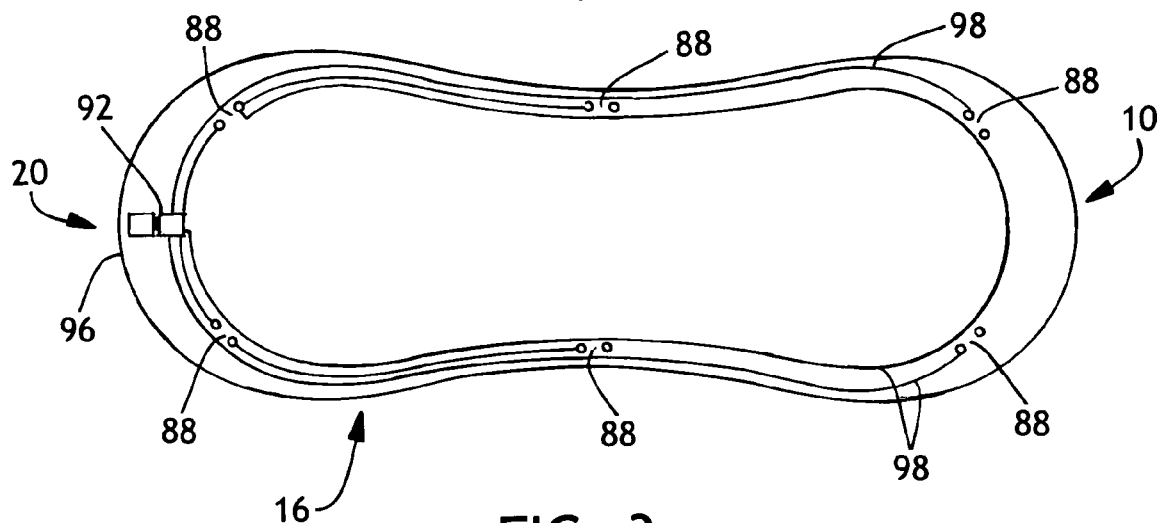
FIG. 3 representatively illustrates a plan schematic view of a particular aspect of the leakage warning element viewed from the bottom as used in conjunction with the feminine/incontinence pad of FIG. 1.

In one aspect of the present application illustrated in FIGS. 2 and 3, the leakage warning element 20 includes a pair of parallel conductive sensor traces 80 positioned largely adjacent the perimeter 65. While FIGS. 2 and 3 exhibit an example of the positioning of such traces 80, any suitable positioning can be used.

More specifically, the leakage warning element 20 can include a colorless, translucent, thin and very flexible circuit substrate 84 in the size and shape as depicted in FIG. 2. The circuit substrate 84 of FIG. 2 includes pair of sensor traces 80 and from one set to six or more sets of electrode pairs 88. The bottom of the circuit substrate is shown in FIG. 3 and includes an electronic processor 92, a battery 96, and the connection traces 98 required to make the circuit operate.

Figure 4:
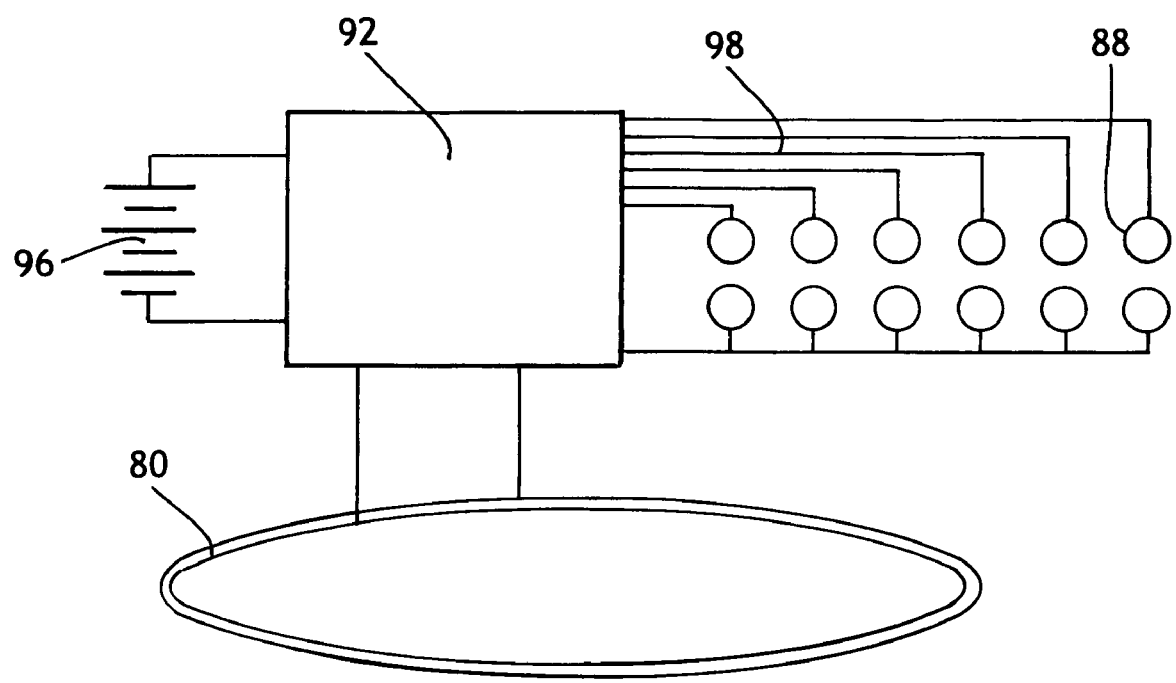
FIG. 4 representatively illustrates a circuit schematic view of a particular aspect of the leakage warning element as used in conjunction with the feminine/incontinence pad of FIG. 1.

FIG. 4 illustrates the circuit in a circuit schematic format. The battery 96 is mounted to the underside of the circuit substrate 84. This battery 96 supplies power to the processor chip 92 as well as to the electrode pairs 88 via the sensor traces 80.

The processor chip 92 is also mounted to the underside of the circuit substrate 84 and monitors conductivity across the pair of sensor traces 80. The processor chip 92 is also adapted to provide a monitored current to the electrode pairs 88. This current is controlled by the processor chip 92. All common points of the electrode pairs 88 share a common lead from the processor chip 92. All electrode pairs 88 also have unique connection traces 98 connected to the processor chip 92 so that the current across an electrode pair 88 can be monitored by the processor chip 92.

The pair of sensor traces 80 are positioned on the top side of the circuit substrate 84 and are connected to the processor chip 92. The pair of sensor traces 80 are located in close proximity to each other such that a fluid passing between adjacent sensor traces 80 provides a path for conductance between the sensor traces 80. Such conductance is sensed by the processor chip 92. The presence of such a conductance triggers the processor chip 92 to release electrical current to the electrode pairs 88.

The circuit further includes connection traces 98 on the underside of the circuit substrate 84 to transmit current to the electrode pairs 88. As stated above, one connection trace 98 will be common to all electrode pairs 88, and one of each of the other connection traces 98 will be unique to each of the other electrode pairs 88.

The electrode pairs 88 are positioned on the top side of the circuit substrate 84. It should be noted that the circuit components can be positioned on a circuit substrate 84 or can otherwise be positioned on a component of the article in which they are resident.

With respect to operation of the circuit, if liquid bridges the sensor traces 80 at any point, the electronic processor 92 detects the change in conductivity between the pair of sensor traces 80. The processor 92 then develops a flow of direct current between each electrode pair 88. The current flow between each electrode pair 88 is controlled independently. The current flow is maintained for ten seconds and then is discontinued for ten seconds. This cycle repeats for a total time of sixty seconds. In other aspects, the on and off timing and the cycle length can be varied as desired. Once the cycle is completed, the circuit no longer needs to function.

The controlled current between each electrode pair 88 is typically between 0.001 and 0.005 amperes with a target value of 0.003 amperes, although the range and particular target value can be suitably varied as desired. The contact resistance between the electrode pairs 88 when the feminine/incontinence pad 16 is in a dry or unused state is desirably in the range of 1,000,000 to 20,000,000 ohms with a target resistance value of 5,000,000 ohms, although any suitable resistance value or range can be used.

The material and coating selected for the electrode pairs 88, as well as the contact pressure on the electrode pairs 88, will have an effect on the resistance between pairs 88. The electrode pairs 88 are positioned on the feminine/incontinence pad 16 such that at least one of the electrode pairs 88 maintains contact with the body of the wearer of the feminine/incontinence pad 16. The electrode pairs 88 can be positioned to project through the bodyside liner 64 to allow better contact with the wearer's body. Maintaining such body contact ensures that the resistance between the contacts of an electrode pair 88 is lower through the body than it is through the air or through the material between the contacts of an electrode pair 88. As a result, the current path between the contacts of an electrode pair 88 will be through the body, allowing the wearer to feel a physical sensation.

In other aspects of the present disclosure, the contacts of the electrode pairs 88 can be partially coated, shielded, or otherwise suitably insulated to ensure that any current flow is through the body of the wearer. The contacts of the electrode pairs 88 can also be electrically separated by added insulation material between the contacts. In another aspect of the present disclosure, the material between the contacts of an electrode pair 88 can be treated with a hydrophobic substance, or not treated with a hydrophilic substance, such that bodily fluid or other moisture will not create a current path through or along the material between the contacts. In other aspects of the present disclosure, the contacts can be manufactured in a composite manner such that the tips, and not the sides, of the contacts conduct electricity.

Any suitable battery 96 can be used, including standard watch-type batteries, printed batteries, and the like. The battery 96 should have a minimum shelf life of two years and still be able to perform the intended function.

Figure 5:
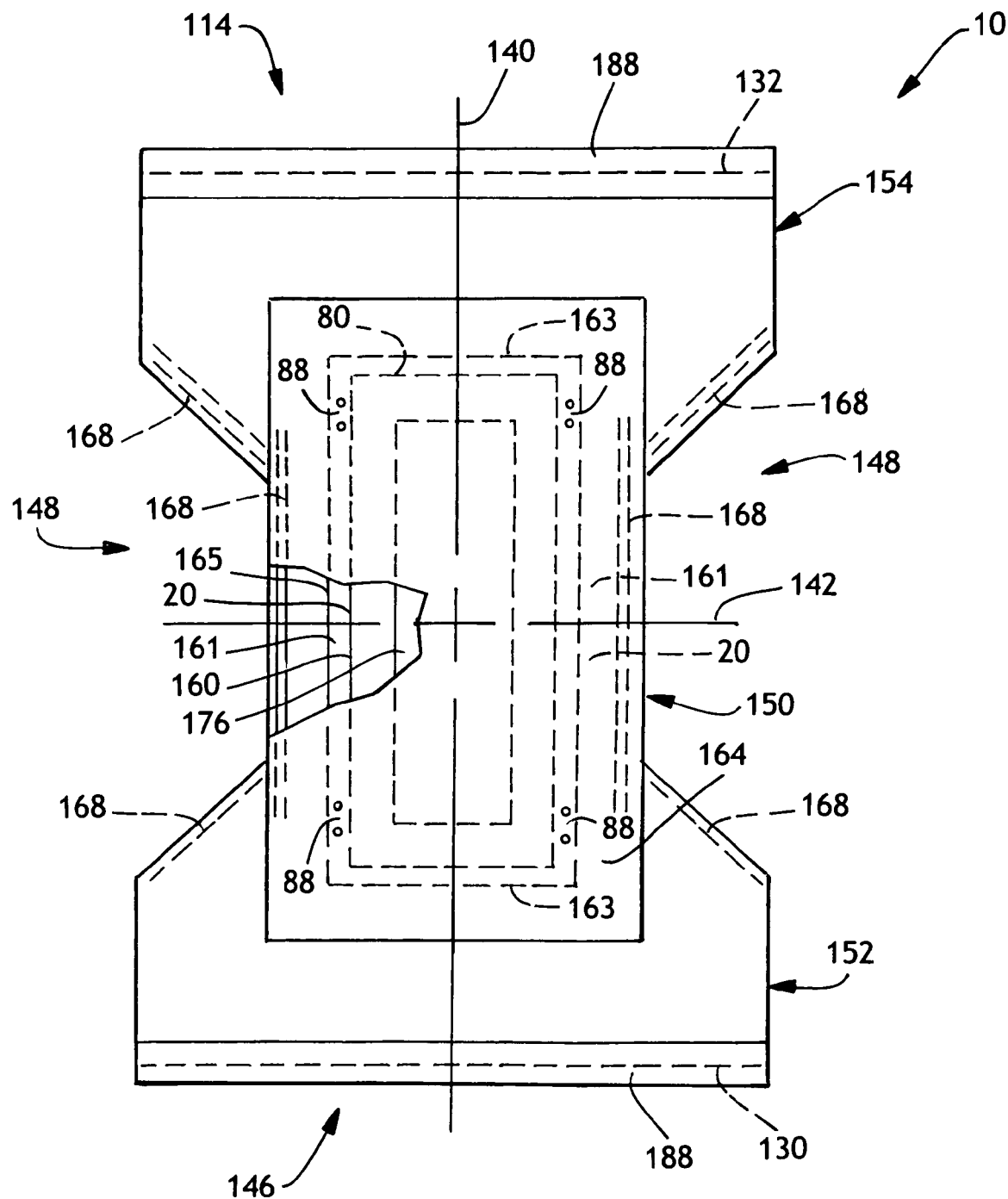
FIG. 5 representatively illustrates a plan view of a particular aspect of an adult garment of the present disclosure.

Referring to FIG. 5, a disposable pant-like absorbent adult undergarment 114 is depicted. The undergarment 114 is designed to be pulled up around a wearer's torso without having to first open the undergarment 114 to place it on a wearer's body. In FIG. 5, the undergarment 114 is shown as it would appear after it has been removed from the package but before it is pulled up around a wearer's torso.

The undergarment 114 has a longitudinal axis 140 and a transverse axis 142. The undergarment 114 includes a front waist region 152, a back waist region 154 and a crotch region 150. The crotch region 150 joins the front waist region 152 to the back waist region 154. The front and back regions 152 and 154 can be stretchable. By "stretchable" it is meant that the regions 152 and 154 can be increased in size, for example lengthened, widened or extended in one or more dimensions by applying a force, such as by pulling. The crotch region 150 can be stretchable or non-stretchable but desirably is non-stretchable.

The front waist region 152 has a front end edge 130 and the back waist region 154 has a back end edge 132. The undergarment 114 can be folded approximately along the transverse axis 142 such that the front end edge 130 aligns with the back end edge 132.

The front waist region 152 and the back waist region 154 are shown as being separate and discontinuous from one another although the front, back and crotch regions 152, 154, and 150 could be formed from a single piece of material, if desired. Desirably, the front waist region 152 is formed from a similar or identical material as the back waist region 154. The undergarment 114 has an bodyside liner 164 and an outercover (not shown). The liner 164 will be in direct contact with the wearer's skin when the undergarment 114 is worn. The outercover or garment-facing surface will be spaced away from the wearer's skin and will be adjacent to any outer clothing that the wearer can be wearing.

The front and back waist regions 152 and 154 can be constructed from various materials. The material can be a single layer or be a laminate of two or more layers. Spunbond is a material that works well for the front and back waist regions 152 and 154. Spunbond is a nonwoven material that is capable of being stretched at least a minimum amount.

Other options for the front and back waist regions 152 and 154 can include two outer layers having a plurality of elastic strands sandwiched therebetween.

The undergarment 114 also includes an absorbent assembly 160 present in the crotch region 150. The absorbent assembly 160 can include a liquid pervious bodyside cover, a liquid-impervious backsheet, and an absorbent positioned therebetween. The absorbent in the absorbent assembly 160 can be formed from natural or synthetic materials. The absorbent can be made from cellulosic fibers, wood pulp, textile fibers or from other absorbent materials known to those skilled in the art. Superabsorbents, commonly in solid form and in the shape of small particles, granules, flakes, etc., can be mixed, combined, attached, printed or otherwise added to the absorbent material to increase the absorbent capacity of the absorbent. A surge layer 176 can also be optionally used, which is normally positioned between the bodyside liner 164 and the absorbent assembly 160. The surge layer 176 can function to rapidly acquire and temporarily retain body fluid, such as urine, before it can be absorbed into the absorbent. Desirably, the surge layer 176 is also capable of wicking body fluid lengthwise and/or widthwise across its surface as well as directing the body fluid downward in a z-direction, toward the absorbent.

The undergarment 114 further includes a waistband 188 secured to the front and back end edges 130 and 132. A portion of the waistband 188 overlaps each of the front and back waist regions 152 and 154 and projects outward therefrom. The waistband 188 can be described as extending outward from the front and back end edges 130 and 132 in a cantilevered configuration.

The waistband 188 can be constructed from almost any elastic material having stretch and retraction capabilities. A desirable nonwoven material from which the waistband 188 can be constructed is spunbond. The waistband 188 can be a laminate containing a first layer, a second layer and two or more elastic strands positioned therebetween. The outer two layers can be constructed or formed from a woven or a non-woven material, a natural or synthetic material, an elastic film, a thermoplastic film, or from any other material known to those skilled in the art. The number of elastic strands positioned between the two outer layers can vary depending upon the width of the waistband 188.

The undergarment 114 further includes a pair of side seams (not shown) which function to join, bond and/or secure the front waist region 152 to the back waist region 154. The pair of side seams extend through the waistband 188 as well to form a unitary undergarment. By "unitary" it is meant that the undergarment 114 is designed to be stepped into by a wearer and the undergarment 114 is then pulled up along the wearer's legs and thighs and positioned around the wearer's torso. There is no need to first open a unitary undergarment before it is applied to a wearer's body. The unitary undergarment 114 has a longitudinal axis 140, a waist opening 146, and a pair of leg openings 148.

The undergarment 114 further includes leg elastic members 168, each of which at least partially surrounds the pair of leg openings 148. The elastic members 168 can consist of one or more elastic strands. Each of the elastic members 168 can be formed as a continuous or a non-continuous member. In FIG. 5, each of the elastic members 168 is depicted as two separate and distinct members that are spaced apart from one another. However, a single elastic member 168, consisting of two or three elastic strands, could be employed to extend from one side seam to the opposite side seam.

The undergarment 114 can also include leg cuffs or leg flaps, each of which at least partially surrounds the pair of leg openings 148, to better seal the leg openings 148 against leakage (not shown). The leg cuffs can also include elastic members consisting of one or more elastic strands. Each of the elastic members can be formed as a continuous or a non-continuous member.

The absorbent assembly 160 can be in a variety of shapes and configurations as are known in the art, such as rectangular, hourglass shaped, I-shaped, and the like. The absorbent assembly 160 has opposed lateral edges 161 and opposed longitudinal ends 163. The lateral edges 161 and longitudinal ends 163 together make up the perimeter 165 of the absorbent assembly 60.

The leakage warning element 20 including a pair of sensor traces 80 and pairs of electrodes 88 is positioned within the adult garment 114 so that urine or other body exudates filling the absorbent assembly 160 contacts the leakage warning element 20 prior to completely filling and eventually leaking from the adult garment 114. Thus, the leakage warning element 20 is disposed with or near the absorbent assembly 160 so that urine or other body exudates contacting the absorbent assembly will also eventually contact the leakage warning element 20. Most desirably, the leakage warning element 20 is disposed on the bodyside of the absorbent assembly 160 so as to be sandwiched between the absorbent assembly 160 and the bodyside liner 164. In this way, the physical sensation resulting from the leakage warning element 20 is more easily noticed by the wearer. The electrode pairs 88 can be positioned to project through the bodyside liner 164 to allow better contact with the wearer's body.

Alternatively, however, the leakage warning element 20 can be located within the absorbent assembly 160 or beneath the absorbent assembly 160 (not shown). The leakage warning element 20 can also be positioned on the leg cuffs or containment flaps or in any other suitable position in the adult garment 114, as long as fluid communication is provided between the absorbent assembly 160 and the leakage warning element 20. Leakage warning elements 20 can be positioned on the flaps, positioned as a single web at the center of the flaps, slit with the flaps, or placed at the flap base. The leakage warning element 20 can also be placed near the flap elastic members so that the substances are encapsulated in the flap material, not allowing the particle material to fall out. In addition, leakage warning elements 20 can be positioned in more than one location within the adult garment 114. The leakage warning element 20 can be bonded in position using adhesives, ultrasonic bonds, or other suitable means.

As illustrated in FIG. 5, portions of the leakage warning element 20 are positioned on opposite sides of the longitudinal axis 140 and spaced apart from the intersection of the longitudinal and transverse axes 140, 142 along the transverse axis 142. Similarly, portions of the leakage warning element 20 can be positioned on opposite sides of the transverse axis 142 and spaced apart from the intersection of the longitudinal and transverse axes 140, 142 along the longitudinal axis 140.

Figure 6:
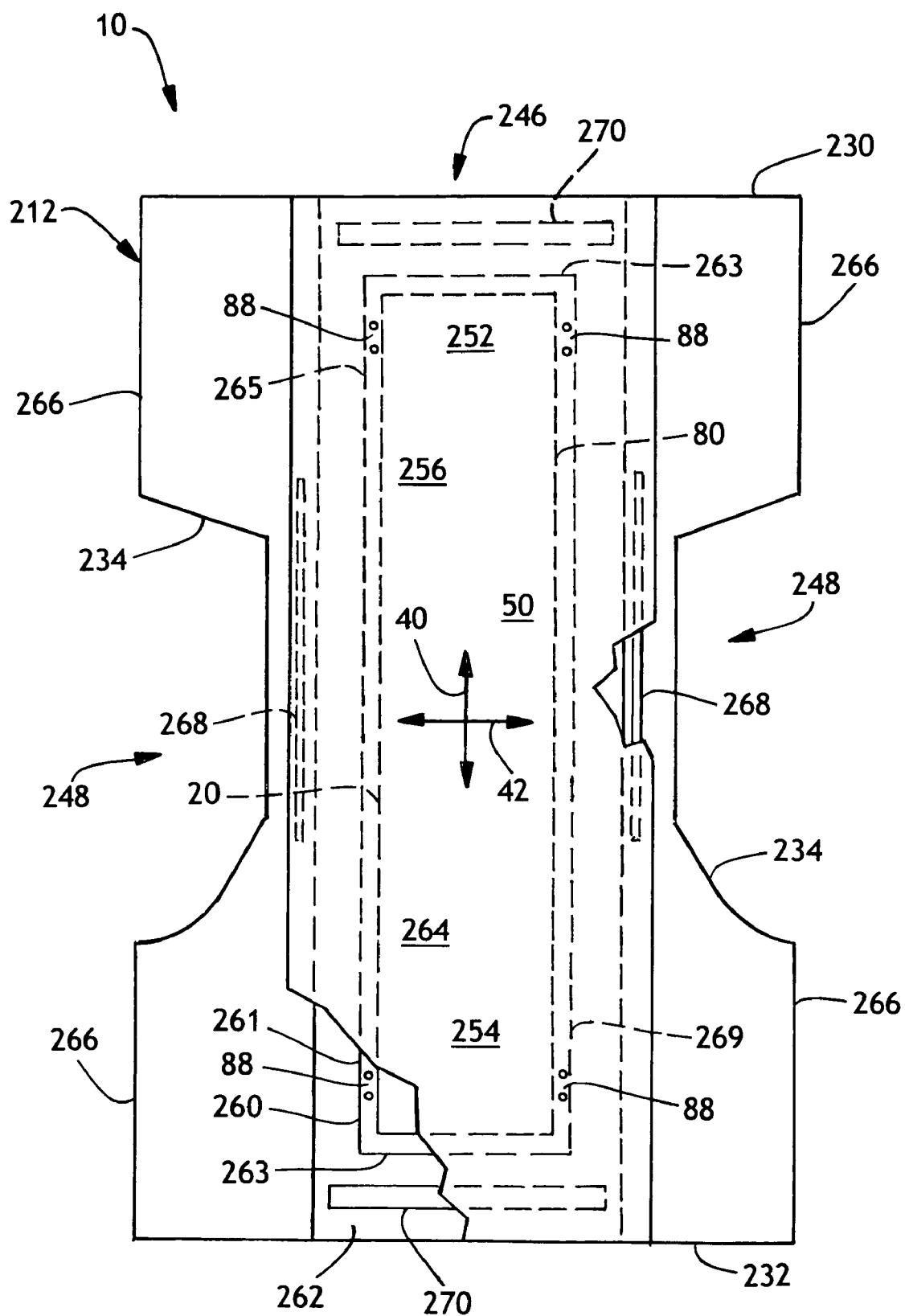
FIG. 6 representatively illustrates a plan view of a number of aspects of a pair of training pants showing the surface of the training pants that faces the wearer when worn, and with portions cut away to show underlying features.

Referring now to the drawings and in particular to FIG. 6, an absorbent article 10 of the present disclosure is representatively illustrated in the form of children's toilet training pants and is indicated in its entirety by the reference numeral 212. The absorbent article 10 includes a leakage warning element 20 including a pair of sensor traces 80 and pairs of electrodes 88 that is adapted to create a distinct physical sensation to the wearer upon the absorbent article 10 nearing fullness, which can enhance a wearer's ability to recognize when leakage can be a threat With reference to FIG. 6, an absorbent article 10 formed according to the disclosure is shown for purposes of illustration as a disposable training pant 212 for use by a child. The training pant 212 includes a leakage warning element 20 that is positioned and adapted to create a distinct physical sensation as the training pant 212 approaches fullness. Because the physical sensation is noticeable to the child, the child's ability to recognize when fullness is occurring will be enhanced. The training pant 212 will now be described in greater detail.

The training pant 212 is illustrated at an intermediate stage of assembly and in a flat and stretched condition in FIG. 6. The training pant 212 has opposite longitudinally spaced front and back end edges 230 and 232, and opposite side edges 234 extending between the end edges. The training pant 212 also defines longitudinal and transverse axes represented by arrows 240 and 242 in FIG. 6.

The finished training pant 212 becomes three-dimensional and thus defines a waist opening 246 and two leg openings 248 (FIG. 6). The finished training pant 212 has a crotch region 250 generally located between the leg openings 248. The crotch region 250 includes that portion of the training pant 212 which, when worn, is positioned between the legs of the wearer and covers the lower torso of the wearer. A front waist region 252 of the training pant 212 extends generally from the crotch region 250 to the front end edge 230, and a back waist region 254 extends from the crotch region 250 to the back end edge 232. In general, the longitudinal extent of the waist regions 250 and 252 is related to the distance between the end edges 230 and 232 of the training pant 212 and the crotch region 250, measured along the side edges 234. The training pant 212 also includes an inner surface 256 and an opposite outer surface (not shown).

With particular reference to FIG. 6, the illustrated training pant 212 includes an absorbent assembly 260 sandwiched between an outercover 262 and a bodyside liner 264. The outercover 262 and liner 264 are desirably longer and wider than the absorbent assembly 260 and bonded together using adhesives, thermal bonds, ultrasonic bonds or other suitable means. Further, the absorbent assembly 260 is disposed on the outercover 262, and can be bonded directly thereto using adhesives, thermal bonds, ultrasonic bonds or other suitable means. The liner 264 maybe bonded directly to the absorbent assembly 260 as well.

The outercover 262 may, for instance, include a single layer of film, a woven material, a nonwoven material or another suitable liquid permeable or liquid impermeable material. The outercover 262 can include a thin, substantially liquid impermeable web or sheet of plastic film such as polyethylene, polypropylene, polyvinyl chloride or similar material. Alternatively, the outercover 262 can include a nonwoven, fibrous web which has been suitably constructed and arranged to be substantially liquid impermeable. Still alternatively, the outercover 262 can include a layered or laminated material, such as a thermally bonded plastic film and nonwoven web composite or a stretch bonded laminate.

The outercover 262 can suitably include a material that is substantially liquid impermeable. The outercover 262 can be provided by a single layer of liquid impermeable material, or more suitably include a multi-layered laminate structure in which at least one of the layers is liquid impermeable. In particular aspects, the outer layer can suitably provide a relatively cloth-like texture to the wearer. A suitable liquid impermeable film for use as a liquid impermeable inner layer, or a single layer liquid impermeable outercover 262 is a 0.025 millimeter (1.0 mil) polyethylene film. Alternatively, the outercover 262 can include a woven or non-woven fibrous web layer that has been totally or partially constructed or treated to impart the desired levels of liquid impermeability to selected regions that are adjacent or proximate the absorbent assembly.

The outercover 262 can also be stretchable, and in some aspects it can be elastomeric. For example, such an outercover material can include a 0.3 osy polypropylene spunbond that is necked 60 percent in the transverse direction 242 and creped 60 percent in the longitudinal direction 240, laminated with 3 grams per square meter (gsm) styrene-isoprene-styrene based adhesive to 8 gsm PEBAX 2533 film with 20 percent $TiO_2$ concentrate.

The bodyside liner 264 can be any soft, flexible, porous sheet that passes liquids therethrough. The liner 264 can include, for example, a nonwoven web or sheet of wet strength tissue paper, a spunbonded, meltblown or bonded-carded web composed of synthetic polymer filaments, such as polypropylene, polyethylene, polyesters or the like, or a web of natural polymer filaments such as rayon or cotton. The liner 264 has a pore size that readily allows the passage therethrough of liquids, such as urine and other body exudates. The liner 264 can be selectively embossed or perforated with discrete slits or holes extending therethrough. Optionally, the web or sheet can be treated with a surfactant to aid in liquid transfer.

Alternatively, the bodyside liner 264 can also be stretchable, and in some aspects it can be elastomeric. For instance, the liner 264 can be a non-woven, spunbond polypropylene fabric composed of about 2 to 3 denier fibers formed into a web having a basis weight of about 12 gsm which is necked approximately 60 percent. Strands of about 9 gsm elastomer material placed eight strands per inch (2.54 cm) can be adhered to the necked spunbond material to impart elasticity to the spunbond fabric. The fabric can be surface treated with an operative amount of surfactant. Other suitable materials can be extensible biaxially stretchable materials, such as a neck stretched/creped spunbond.

The absorbent assembly 260 can be in a variety of shapes and configurations as are known in the art, such as rectangular, hourglass shaped, I-shaped, and the like. The absorbent assembly 260 has opposed lateral edges 261 and opposed longitudinal ends 263. The lateral edges 261 and longitudinal ends 263 together make up the perimeter 265 of the absorbent assembly 260.

The absorbent assembly 260 can include various absorbent materials, such as an air-formed batt of cellulosic fibers (i.e., wood pulp fluff) or a coform material composed of a mixture of cellulosic fibers and synthetic polymer fibers. The absorbent assembly 260 can also include compounds to increase its absorbency, such as 0-95 weight percent of organic or inorganic high-absorbency materials, which are typically capable of absorbing at least about 15 and desirably more than 25 times their weight in water. The absorbent assembly 260 can also include tissue layers or acquisition or distribution layers to help maintain the integrity of fibrous absorbents or transport liquids (not shown).

The absorbent assembly 260 is suitably compressible, conformable, and capable of absorbing and retaining liquid body exudates released by the wearer. For example, the absorbent assembly can include a matrix of absorbent fibers, and more suitably cellulosic fluff, such as wood pulp fluff, and superabsorbent particles. As an alternative to wood pulp fluff, synthetic fibers, polymeric fibers, meltblown fibers, short cut homofil bicomponent synthetic fibers, or other natural fibers can be used. Suitable superabsorbent materials can be selected from natural, synthetic, and modified natural polymers and materials. The superabsorbent materials can be inorganic materials, such as silica gels, or organic compounds, such as crosslinked polymers, for example, sodium neutralized polyacrylic acid.

In one aspect, the absorbent assembly 260 can be stretchable so as not to inhibit the stretchability of other components to which the absorbent assembly can be adhered, such as the outercover 262 and/or the bodyside liner 264.

In some aspects, a surge management layer (not shown) can be included in the training pants 212. The surge management layer can be positioned in the training pants 212 in a variety of locations as is known in the art. For example, the surge management layer can be proximate the absorbent assembly 260, for example between the absorbent assembly 260 and the bodyside liner 264, and attached to one or more components of the training pants 212 by methods known in the art, such as by adhesive, ultrasonic or thermal bonding. In addition, the surge management layer can be positioned in the training pants 212 relative to the leakage warning element 20 in a variety of ways. For instance, the surge management layer can be disposed toward the liner 264 relative to the leakage warning element 20, or the surge management layer can be disposed toward the absorbent assembly 260 relative to the leakage warning element 20.

A surge management layer helps to decelerate and diffuse surges or gushes of liquid that can be rapidly introduced into the absorbent assembly 260. Desirably, the surge management layer can rapidly accept and temporarily hold the liquid prior to releasing the liquid into the storage or retention portions of the absorbent assembly 260.

The training pant 212 also includes a pair of side panels 266. Each side panel 266 is positioned transversely outward from the absorbent assembly 260 and bonded to the outercover 262, the bodyside liner 264, or both using adhesives, thermal bonds, ultrasonic bonds or other suitable means.

The side panels 266 are desirably formed of an elastic material capable of stretching in a direction parallel to the transverse axis 242 of the training pant 212. Further, the side panels 266 can also be formed of a gas permeable material, referred to as breathable material. The side panels 266 may, for instance, comprise a single layer of apertured film, a woven material, a nonwoven material or another suitable liquid permeable or liquid impermeable material. The side panels 266 can also comprise a laminate material, such as a stretch bonded laminate formed of a prestretched elastic meltblown inner layer sandwiched between and attached to a pair of spunbond polypropylene nonwoven webs having a basis weight of about 13.6 grams per square meter.

In one aspect, the side panels 266 are formed of a laminated material including a prestretched elastic meltblown inner layer having a basis weight of about 18 grams per square meter (gsm) sandwiched between and stretch bonded to a pair of spunbond webs each having a basis weight of about 14.9 gsm. The spunbond webs comprise bicomponent fibers formed of about 50 weight percent polypropylene and about 50 weight percent polyethylene in a side-by-side configuration. Alternately, suitable elastic strands can be substituted for the elastic meltblown layer.

The training pant 212 can also include leg elastic members 268 and waist elastic members 270 that are bonded to the outercover 262, the bodyside liner 264, or both to enhance fit and performance (FIG. 6). In particular, the leg elastic members 268 are operatively joined to the outercover 262 along each side edge 234 through the crotch region 250. Also, the waist elastic members 270 are operatively joined to the outercover 262 along the front and back end edges 230 and 232. The elastic members 268 and 270 can be bonded in place using adhesives, thermal bonds, ultrasonic bonds, stitching, or other suitable means. The elastic members 268 and 270 can be stretch bonded to the outercover 262, bonded in a relaxed state to a gathered portion of the outercover, or a combination of the two.

The training pant 212 can further include a pair of containment flaps (not shown) for inhibiting the lateral flow of body exudates. Containment flaps can be operatively attached to the training pant 212 in any suitable manner as is well known in the art. In particular, suitable constructions and arrangements for the containment flaps are generally well known to those skilled in the art.

As illustrated in FIG. 6, the leakage warning element 20 can be positioned in the training pant 212. Because the training pant 212 is most likely to be in contact with the wearer in the region of the wearer's abdomen, the leakage warning element 20 desirably includes positioning in the front waist region 252 and more particularly in the front one third of the length of the training pant 212. Alternatively, leakage warning element 20 can include positioning in the back waist region 254, such as in the back one third of the length of the training pant 212.

The leakage warning element 20 including a pair of sensor traces 80 and pairs of electrodes 88 is positioned within the training pant 212 so that urine or other body exudates filling the absorbent assembly 260 contacts the leakage warning element 20 prior to completely filling and eventually leaking from the training pant 212. Thus, the leakage warning element 20 is disposed with or near the absorbent assembly 260 so that urine or other body exudates contacting the absorbent assembly will also eventually contact the leakage warning element 20. Most desirably, the leakage warning element 20 is disposed on the bodyside of the absorbent assembly 260 so as to be sandwiched between the absorbent assembly 260 and the bodyside liner 264. In this way, the physical sensation resulting from the leakage warning element 20 is more easily noticed by the wearer. The electrode pairs 88 can be positioned to project through the bodyside liner 264 to allow better contact with the wearer's body.

Alternatively, however, the leakage warning element 20 can be located within the absorbent assembly 260 or beneath the absorbent assembly 260 (not shown). The leakage warning element 20 can also be positioned on the containment flaps or in any other suitable position in the training pant 212, as long as fluid communication is provided between the absorbent assembly 260 and the leakage warning element 20. Leakage warning elements 20 can be positioned on the flaps, positioned as a single web at the center of the flaps, slit with the flaps, or placed at the flap base. The leakage warning element 20 can also be placed near the flap elastic members so that the substances are encapsulated in the flap material, not allowing the particle material to fall out. In addition, leakage warning elements 20 can be positioned in more than one location within the training pant 212. The leakage warning element 20 can be bonded in position using adhesives, ultrasonic bonds, or other suitable means.

Aspects of the disclosure have been described with reference to various specific and illustrative aspects and techniques. However, it should be understood that many variations and modifications can be made while remaining within the spirit and scope. Accordingly, this is intended to embrace all such alternatives, modifications and variations that fall within the spirit and scope of the appended claims. As various changes could be made in the above constructions and methods, without departing from the scope of the disclosure, it is intended that all matter contained in the above description and shown in the accompanying drawings shall be interpreted as illustrative and not in a limiting sense.

When introducing elements of the disclosure or the preferred aspect(s) thereof, the articles "a", "an", "the" and "said" are intended to mean that there are one or more of the elements. The terms "comprising," "including," and "having" are intended to be inclusive and mean that there can be additional elements other than the listed elements.

What is claimed is:

1. An absorbent article for preventing leakage, the article comprising:
    an absorbent assembly having an absorbent assembly perimeter; and
    a leakage warning element disposed adjacent a portion of the perimeter, wherein the leakage warning element is adapted to provide a physical sensation indicating a fullness level of the absorbent assembly, and wherein the physical sensation includes an electrical current delivered to a wearer of the article.

2. The article of claim 1, wherein the absorbent assembly has a lateral edge, and wherein the portion of the perimeter is the lateral edge.

3. The article of claim 1, wherein the absorbent assembly has a longitudinal end, and wherein the portion of the perimeter is the longitudinal end.

4. The article of claim 1, the absorbent assembly has a longitudinal axis, and wherein the leakage warning element is spaced apart from the longitudinal axis.

5. The article of claim 1, the absorbent assembly has a transverse axis, and wherein the leakage warning element is spaced apart from the transverse axis.

6. The article of claim 1, wherein the leakage warning element includes an electrical circuit.

7. The article of claim 6, wherein the electrical circuit includes a battery.

8. The article of claim 6, wherein the electrical circuit includes a pair of electrodes adapted to provide a physical sensation.

9. The article of claim 8, wherein the pair of electrodes is adapted to remain in contact with a body of a wearer when the article is being worn.

10. The article of claim 6, wherein the electrical circuit includes a conductor disposed on a circuit substrate, and wherein the circuit substrate is disposed on the absorbent assembly.

11. The article of claim 6, wherein the electrical circuit includes a conductor disposed on a circuit substrate, and wherein the circuit substrate is disposed adjacent a portion of the perimeter.

12. The article of claim 1, wherein the article is a garment-like article including leg openings, and wherein the leakage warning element is disposed adjacent the leg openings.

13. The article of claim 1, the article further including a flap, wherein the portion of the perimeter is the flap.

14. The article of claim 1, the article further including a cuff, wherein the portion of the perimeter is the cuff.

15. The article of claim 1, the article further including a tab, wherein the portion of the perimeter is the tab.

16. An absorbent article for providing a wearer with a warning of potential leakage, the article comprising:
    an absorbent assembly; and
    a leakage warning element disposed adjacent the absorbent assembly, wherein the leakage warning element is adapted to impart a physical sensation to the wearer, and wherein the physical sensation includes an electrical current delivered to the wearer of the article.

17. The article of claim 16, wherein the leakage warning element includes an electrical circuit.

18. The article of claim 17, wherein the electrical circuit includes a pair of electrodes adapted to provide a physical sensation and adapted to remain in contact with a body of a wearer when the article is being worn.

19. An absorbent article for providing a wearer with a warning of potential leakage, the article comprising:
    an absorbent assembly; and
    a leakage warning element in fluid contact with the absorbent assembly, wherein the leakage warning element is adapted to impart a physical sensation to the wearer, and wherein the physical sensation includes an electrical current delivered to the wearer of the article.

20. The article of claim 19, wherein the leakage warning element includes a pair of electrodes adapted to provide a physical sensation and adapted to remain in contact with a body of a wearer when the article is being worn.

* * * * *